(12) United States Patent
Xu et al.

(10) Patent No.: US 11,330,991 B2
(45) Date of Patent: May 17, 2022

(54) CALIBRATION METHOD FOR BLOOD PRESSURE MEASURING DEVICE, AND BLOOD PRESSURE MEASURING DEVICE

(71) Applicant: Huawei Technologies Co., Ltd., Shenzhen (CN)

(72) Inventors: Peida Xu, Shenzhen (CN); Wenjuan Chen, Shenzhen (CN); Yu Zhu, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 302 days.

(21) Appl. No.: 16/343,384

(22) PCT Filed: Oct. 21, 2016

(86) PCT No.: PCT/CN2016/102947
§ 371 (c)(1),
(2) Date: Apr. 18, 2019

(87) PCT Pub. No.: WO2018/072212
PCT Pub. Date: Apr. 26, 2018

(65) Prior Publication Data
US 2019/0313917 A1   Oct. 17, 2019

(51) Int. Cl.
*A61B 5/022* (2006.01)
*A61B 5/021* (2006.01)
(Continued)

(52) U.S. Cl.
CPC .......... *A61B 5/022* (2013.01); *A61B 5/02108* (2013.01); *A61B 5/02416* (2013.01);
(Continued)

(58) Field of Classification Search
CPC .... A61B 2560/0223; A61B 2560/0228; A61B 5/02156; A61B 2560/0247; A61B 5/28;
(Continued)

(56) References Cited

U.S. PATENT DOCUMENTS

| 4,397,317 A | 8/1983 | Villa-Real |
| 5,857,975 A | 1/1999 | Golub |

(Continued)

FOREIGN PATENT DOCUMENTS

| CN | 1237885 A | 12/1999 |
| CN | 101365376 A | 2/2009 |

(Continued)

OTHER PUBLICATIONS

Chin, "A New Approach for Non-Invasive Continuous Arterial Blood Pressure Measurement in Human" (Dissertation), 2011, University of Leicester (Year: 2011).*

*Primary Examiner* — Devin B Henson
*Assistant Examiner* — Justin Xu
(74) *Attorney, Agent, or Firm* — Slater Matsil, LLP

(57) ABSTRACT

A method for calibrating a blood pressure measurement device includes obtaining first blood pressure measurement information and a current confidence coefficient corresponding to the first blood pressure measurement information, determining the first blood pressure measurement information as blood pressure calibration information in response to the blood pressure measurement device comprising the historical calibration parameter list, and the current confidence coefficient being greater than or equal to a preset confidence coefficient or the historical confidence coefficient, and updating the historical calibration parameter list based on the first blood pressure measurement information and the current confidence coefficient.

17 Claims, 7 Drawing Sheets

(51) Int. Cl.
*A61B 5/024* (2006.01)
*A61B 5/00* (2006.01)

(52) U.S. Cl.
CPC ......... *A61B 5/02141* (2013.01); *A61B 5/6824* (2013.01); *A61B 5/6826* (2013.01); *A61B 2560/0223* (2013.01)

(58) Field of Classification Search
CPC ....... A61B 8/04; A61B 5/021; A61B 5/02108; A61B 5/02116; A61B 5/022; A61B 5/02416; A61B 5/02141; A61B 5/6824; A61B 5/6826; G01L 27/005
USPC .................................................. 600/485, 480
See application file for complete search history.

(56) References Cited

U.S. PATENT DOCUMENTS

| | | |
|---|---|---|
| 9,408,542 B1 | 8/2016 | Kinast et al. |
| 2008/0188733 A1 | 8/2008 | Al-Ali et al. |
| 2009/0036751 A1 | 2/2009 | Lutze et al. |
| 2010/0241011 A1 | 9/2010 | McCombie et al. |
| 2010/0331724 A1 | 12/2010 | Watson et al. |
| 2011/0184268 A1* | 7/2011 | Taub .................. A61B 5/14532 600/365 |
| 2012/0029363 A1* | 2/2012 | Lund .................. A61B 5/02108 600/485 |
| 2012/0136261 A1 | 5/2012 | Sethi et al. |
| 2012/0136605 A1* | 5/2012 | Addison ................ G16H 40/40 702/98 |
| 2012/0238846 A1 | 9/2012 | Myers et al. |
| 2012/0289849 A1 | 11/2012 | Kumar et al. |
| 2014/0012147 A1* | 1/2014 | Li .......................... A61B 5/022 600/494 |
| 2015/0057554 A1 | 2/2015 | Watson et al. |
| 2016/0128644 A1 | 5/2016 | Meier et al. |
| 2016/0198963 A1* | 7/2016 | Addison ............ A61B 5/02125 600/480 |
| 2016/0287110 A1 | 10/2016 | Morris et al. |
| 2017/0042433 A1* | 2/2017 | Noh ...................... A61B 5/1118 |

FOREIGN PATENT DOCUMENTS

| | | |
|---|---|---|
| CN | 101366627 A | 2/2009 |
| CN | 102655814 A | 9/2012 |
| CN | 105324071 A | 2/2016 |
| CN | 105342592 A | 2/2016 |

* cited by examiner

CALIBRATION METHOD FOR BLOOD PRESSURE MEASURING DEVICE, AND BLOOD PRESSURE MEASURING DEVICE

CROSS REFERENCE TO RELATED APPLICATIONS

This application is a National Stage of International Application No. PCT/CN2016/102947, filed on Oct. 21, 2016, which is hereby incorporated by reference in its entirety.

TECHNICAL FIELD

The present invention relates to the field of intelligent terminal technologies, and in particular, to a method for calibrating a blood pressure measurement device and a blood pressure measurement device.

BACKGROUND

In recent years, with development of mobile medical technologies, convenience of monitoring a blood pressure is gradually improved, and national and foreign markets attach increasing importance to monitoring of home blood pressures and dynamic blood pressures. Therefore, accurate and portable blood pressure measurement is extremely necessary and is an important issue that currently attracts much attention from people.

Currently, a cuff-less blood pressure measurement apparatus is mainly used to measure a blood pressure of a user. The cuff-less blood pressure measurement apparatus measures a blood pressure by using a pulse wave transit time without a cuff. This can provide a convenient and comfortable measurement manner for the user. Physiological parameters such as an arterial wall elasticity and a blood density of different persons are different, and relationships between a pulse wave transit time and a blood pressure of different users are different. Therefore, when measuring a blood pressure of a user, the cuff-less blood pressure measurement apparatus may perform calibration on a blood pressure of each user, so as to ensure accuracy of the cuff-less blood pressure measurement apparatus on blood pressure measurement.

However, when the current cuff-less blood pressure measurement apparatus is used to perform calibration on a blood pressure of each user, an extra device (such as a cuff sphygmomanometer or a standard sphygmomanometer) is required to measure a standard blood pressure and input a measured standard blood pressure into the cuff-less blood pressure measurement apparatus to obtain an actual blood pressure of a user. Consequently, costs are relatively high.

SUMMARY OF THE INVENTION

The present invention provides a method for calibrating a blood pressure measurement device and a blood pressure measurement device, so as to ensure accuracy of blood pressure measurement information and avoid using an extra device to implement calibration of the blood pressure measurement information.

According to a first aspect, the present invention provides a method for calibrating a blood pressure measurement device, including obtaining first blood pressure measurement information of the blood pressure measurement device and a current confidence coefficient corresponding to the first blood pressure measurement information, where the first blood pressure measurement information includes a first systolic blood pressure value and/or a first diastolic blood pressure value, determining whether the blood pressure measurement device includes a historical calibration parameter list, where the historical calibration parameter list includes historical blood pressure calibration information and a historical confidence coefficient corresponding to the historical blood pressure calibration information, and the historical blood pressure calibration information includes a historical systolic blood pressure value and/or a historical diastolic blood pressure value, and if the blood pressure measurement device includes the historical calibration parameter list, and the current confidence coefficient is greater than or equal to a preset confidence coefficient, or is greater than or equal to the historical confidence coefficient, determining the first blood pressure measurement information as blood pressure calibration information of the blood pressure measurement device, and updating the historical calibration parameter list based on the first blood pressure measurement information and the current confidence coefficient.

The first blood pressure measurement information that is obtained through direct measurement based on the physiological signal of the user is used as the calibration information, and a non-calibration result is applied to manual calibration measurement. This ensures accuracy of a measured blood pressure, reduces times of using an extra device for manual calibration by the user, and avoids using an extra device to implement calibration of blood pressure measurement information. Consequently, costs of measuring blood pressure information by using the blood pressure measurement apparatus are reduced, and the blood pressure measurement apparatus has a relatively high portability.

In a possible implementation, if the blood pressure measurement device does not include the historical calibration parameter list, obtaining a physiological signal of the blood pressure measurement device, where the physiological signal includes an electrocardiogram signal of a user and/or a pulse wave signal of the user, when the current confidence coefficient is less than the historical confidence coefficient, determining second blood pressure measurement information of the blood pressure measurement device based on the historical blood pressure calibration information and the physiological signal, where the second blood pressure measurement information includes a second systolic blood pressure value and/or a second diastolic blood pressure value, obtaining a current blood pressure difference value between the first blood pressure measurement information and the second blood pressure measurement information, if the current blood pressure difference value is greater than or equal to a preset blood pressure difference value, and the current confidence coefficient is greater than or equal to the preset confidence coefficient, adding 1 to a calibration counter, and when a value of the calibration counter is greater than or equal to a preset value, determining the first blood pressure measurement information as blood pressure calibration information of the blood pressure measurement device, resetting the calibration counter, and updating the historical calibration parameter list based on the first blood pressure measurement information and the current confidence coefficient.

When the current confidence coefficient of the first blood pressure measurement information is less than the historical confidence coefficient of the historical blood pressure calibration information, it is determined whether the difference value between the first blood pressure measurement information and the second blood pressure measurement information is greater than the preset blood pressure value, and it is determined whether the current confidence coefficient of the first blood pressure measurement information is greater than a preset threshold, so as to determine whether accuracy of the first blood pressure measurement information measured by the non-calibration measurement module is higher than accuracy of the second blood pressure measurement information measured by the calibration measurement module. Therefore, availability of using the first blood pressure measurement information as the calibration information is determined.

In another possible implementation, the current blood pressure difference value between the first blood pressure measurement information and the second blood pressure measurement information may be obtained in the following feasible implementations. A feasible implementation may be determining the current blood pressure difference value based on the first systolic blood pressure value and the second systolic blood pressure value. Another feasible implementation may be determining the current blood pressure difference value based on the first diastolic blood pressure value and the second diastolic blood pressure value. Still another feasible implementation may be determining the current blood pressure difference value based on a ratio of the first systolic blood pressure value to the first diastolic blood pressure value, and a ratio of the second systolic blood pressure value to the second diastolic blood pressure value.

In another possible implementation, the obtaining a current confidence coefficient corresponding to the first blood pressure measurement information includes obtaining the current confidence coefficient based on at least one of the following parameters input blood pressure data of the blood pressure measurement device, signal quality of the physiological signal of the blood pressure measurement device, historically input blood pressure data of the blood pressure measurement device, or historical physiological signal data of the blood pressure measurement device. The current confidence coefficient corresponding to the first blood pressure measurement information is obtained based on the foregoing at least one parameter, so as to more accurately determine availability of using the first blood pressure measurement information as the calibration information.

In another possible implementation, the obtaining a current confidence coefficient corresponding to the first blood pressure measurement information includes obtaining a first confidence coefficient based on the signal quality of the physiological signal, obtaining a second confidence coefficient based on a difference between the first blood pressure measurement information and the historical blood pressure calibration information, obtaining a third confidence coefficient based on similarity between the input blood pressure data of the blood pressure measurement device and the historically input blood pressure data of the blood pressure measurement device, and obtaining the current confidence coefficient of the first blood pressure measurement information by performing weighted summation on the first confidence coefficient, the second confidence coefficient, and the third confidence coefficient.

The current confidence coefficient corresponding to the first blood pressure measurement information is obtained in the implementation of calculating the current confidence coefficient of the first blood pressure measurement information based on the input blood pressure data, the physiological signal, and the first blood pressure measurement information, so as to ensure availability of using the first blood pressure measurement information as the calibration information.

According to a second aspect, the present invention provides a blood pressure measurement device, including a first obtaining module, a confidence coefficient calculation module, a determining module, and a calibration updating module, where the first obtaining module is configured to obtain first blood pressure measurement information of the blood pressure measurement device, where the first blood pressure measurement information includes a first systolic blood pressure value and/or a first diastolic blood pressure value, the confidence coefficient calculation module is configured to obtain a current confidence coefficient corresponding to the first blood pressure measurement information, the determining module is configured to determine whether the blood pressure measurement device includes a historical calibration parameter list, where the historical calibration parameter list includes historical blood pressure calibration information and a historical confidence coefficient corresponding to the historical blood pressure calibration information, and the historical blood pressure calibration information includes a historical systolic blood pressure value and/or a historical diastolic blood pressure value, and the calibration updating module is configured to, when the determining module determines that the blood pressure measurement device includes the historical calibration parameter list, and the current confidence coefficient is greater than or equal to a preset confidence coefficient, or is greater than or equal to the historical confidence coefficient, determine the first blood pressure measurement information as blood pressure calibration information of the blood pressure measurement device, and update the historical calibration parameter list based on the first blood pressure measurement information and the current confidence coefficient.

The blood pressure measurement device provided in the second aspect of the present invention is configured to perform the technical solution in the method embodiment of the first aspect. The implementation principles and technical effects of the device are similar to those of the technical solution, and are not described herein again.

In a possible implementation, the blood pressure measurement device further includes a second obtaining module, where the second obtaining module is configured to, when the determining module determines that the blood pressure measurement device does not include the historical calibration parameter list, obtain a physiological signal of the blood pressure measurement device, where the physiological signal includes an electrocardiogram signal of a user and/or a pulse wave signal of the user, the first obtaining module is further configured to, when the current confidence coefficient is less than the historical confidence coefficient, determine second blood pressure measurement information of the blood pressure measurement device based on the historical blood pressure calibration information and the physiological signal, where the second blood pressure measurement information includes a second systolic blood pressure value and/or a second diastolic blood pressure value, and the calibration updating module is further configured to obtain a current blood pressure difference value between the first blood pressure measurement information and the second blood pressure measurement information, when the current blood pressure difference value is greater than or equal to a preset blood pressure difference value, and the current confidence coefficient is greater than or equal to the preset confidence coefficient, add 1 to a calibration counter, and when a value of the calibration counter is greater than or equal to a preset value, determine the first blood pressure measurement information as blood pressure calibration information of the blood pressure measurement device, reset the calibration counter, and update the historical calibration parameter list based on the first blood pressure measurement information and the current confidence coefficient.

In another possible implementation, the calibration updating module is specifically configured to determine the current blood pressure difference value based on the first systolic blood pressure value and the second systolic blood pressure value, or determine the current blood pressure difference value based on the first diastolic blood pressure value and the second diastolic blood pressure value, or determine the current blood pressure difference value based on a ratio of the first systolic blood pressure value to the first diastolic blood pressure value, and a ratio of the second systolic blood pressure value to the second diastolic blood pressure value.

In another possible implementation, the confidence coefficient calculation module is specifically configured to obtain the current confidence coefficient based on at least one of the following parameters, including input blood pressure data of the blood pressure measurement device, signal quality of the physiological signal of the blood pressure measurement device, historically input blood pressure data of the blood pressure measurement device, or historical physiological signal data of the blood pressure measurement device.

In another possible implementation, the confidence coefficient calculation module is specifically configured to obtain a first confidence coefficient based on the signal quality of the physiological signal, obtain a second confidence coefficient based on a difference between the first blood pressure measurement information and the historical blood pressure calibration information, obtain a third confidence coefficient based on similarity between the input blood pressure data of the blood pressure measurement device and the historically input blood pressure data of the blood pressure measurement device, and obtain the current confidence coefficient of the first blood pressure measurement information by performing weighted summation on the first confidence coefficient, the second confidence coefficient, and the third confidence coefficient.

The blood pressure measurement device provided in the second aspect of the present invention is configured to perform the technical solution in the method embodiment of the first aspect. The implementation principles and technical effects of the device are similar to those of the technical solution, and are not described herein again.

According to a third aspect, an embodiment of the present invention provides a blood pressure measurement device, including a memory and a processor, where the memory is configured to store an executable instruction, and the processor is configured to invoke the executable instruction in the memory and perform the following operations, including obtaining first blood pressure measurement information of the blood pressure measurement device and a current confidence coefficient corresponding to the first blood pressure measurement information, where the first blood pressure measurement information includes a first systolic blood pressure value and/or a first diastolic blood pressure value, determining whether the blood pressure measurement device includes a historical calibration parameter list, where the historical calibration parameter list includes historical blood pressure calibration information and a historical confidence coefficient corresponding to the historical blood pressure calibration information, and the historical blood pressure calibration information includes a historical systolic blood pressure value and/or a historical diastolic blood pressure value, and if the blood pressure measurement device includes the historical calibration parameter list, and the current confidence coefficient is greater than or equal to a preset confidence coefficient, or is greater than or equal to the historical confidence coefficient, determining the first blood pressure measurement information as blood pressure calibration information of the blood pressure measurement device, and updating the historical calibration parameter list based on the first blood pressure measurement information and the current confidence coefficient.

The blood pressure measurement device provided in the third aspect of the present invention is configured to perform the technical solution in the method embodiment of the first aspect. The implementation principles and technical effects of the device are similar to those of the technical solution, and are not described herein again.

In a possible implementation, the processor is specifically configured to, if the blood pressure measurement device does not include the historical calibration parameter list, obtain a physiological signal of the blood pressure measurement device, where the physiological signal includes an electrocardiogram signal of a user and/or a pulse wave signal of the user, when the current confidence coefficient is less than the historical confidence coefficient, determine second blood pressure measurement information of the blood pressure measurement device based on the historical blood pressure calibration information and the physiological signal, where the second blood pressure measurement information includes a second systolic blood pressure value and/or a second diastolic blood pressure value, obtain a current blood pressure difference value between the first blood pressure measurement information and the second blood pressure measurement information, and if the current blood pressure difference value is greater than or equal to a preset blood pressure difference value, and the current confidence coefficient is greater than or equal to the preset confidence coefficient, add 1 to a calibration counter, and when a value of the calibration counter is greater than or equal to a preset value, determine the first blood pressure measurement information as blood pressure calibration information of the blood pressure measurement device, reset the calibration counter, and update the historical calibration parameter list based on the first blood pressure measurement information and the current confidence coefficient.

In another possible implementation, the processor is specifically configured to determine the current blood pressure difference value based on the first systolic blood pressure value and the second systolic blood pressure value, or determine the current blood pressure difference value based on the first diastolic blood pressure value and the second diastolic blood pressure value, or determine the current blood pressure difference value based on a ratio of the first systolic blood pressure value to the first diastolic blood pressure value, and a ratio of the second systolic blood pressure value to the second diastolic blood pressure value.

In another possible implementation, the processor is specifically configured to obtain the current confidence coefficient based on at least one of input blood pressure data of the blood pressure measurement device, signal quality of the physiological signal of the blood pressure measurement device, historically input blood pressure data of the blood pressure measurement device, or historical physiological signal data of the blood pressure measurement device.

In another possible implementation, the processor is specifically configured to: obtain a first confidence coefficient based on the signal quality of the physiological signal, obtain a second confidence coefficient based on a difference between the first blood pressure measurement information and the historical blood pressure calibration information, obtain a third confidence coefficient based on similarity between the input blood pressure data of the blood pressure measurement device and the historically input blood pressure data of the blood pressure measurement device, and obtain the current confidence coefficient of the first blood pressure measurement information by performing weighted summation on the first confidence coefficient, the second confidence coefficient, and the third confidence coefficient.

The blood pressure measurement device provided in the third aspect of the present invention is configured to perform the technical solution in the method embodiment of the first aspect. The implementation principles and technical effects of the device are similar to those of the technical solution, and are not described herein again.

According to the method for calibrating a blood pressure measurement device and a blood pressure measurement device that are provided in the embodiments of the present invention, the first blood pressure measurement information that is obtained through direct measurement based on the physiological signal of the user is used as the calibration information, and the non-calibration result is applied to manual calibration measurement. This ensures accuracy of a measured blood pressure, reduces times of using an extra device for manual calibration by the user, and avoids using an extra device to implement calibration of blood pressure measurement information. Consequently, costs of measuring blood pressure information by using the blood pressure measurement apparatus are reduced, and the blood pressure measurement device has a relatively high portability.

BRIEF DESCRIPTION OF THE DRAWINGS

To describe the technical solutions in the embodiments of the present invention or in the prior art more clearly, the following briefly describes the accompanying drawings required for describing the embodiments or the prior art. Apparently, the accompanying drawings in the following description show merely some embodiments of the present invention, and a person of ordinary skill in the art may still derive other drawings from these accompanying drawings without creative efforts.

DETAILED DESCRIPTION OF ILLUSTRATIVE EMBODIMENTS

The following clearly and completely describes the technical solutions in the embodiments of the present invention with reference to the accompanying drawings in the embodiments of the present invention. Apparently, the described embodiments are merely some but not all of the embodiments of the present invention. All other embodiments obtained by a person of ordinary skill in the art based on the embodiments of the present invention without creative efforts shall fall within the protection scope of the present invention.

Figure 1:
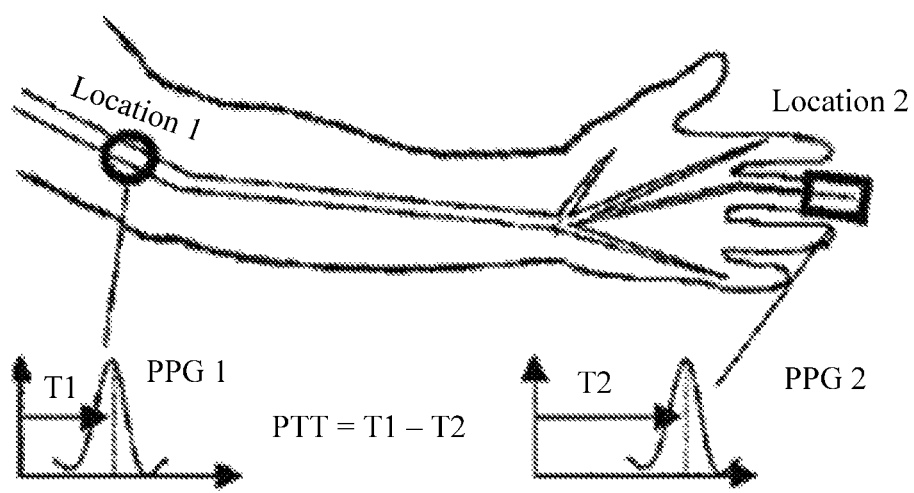
FIG. 1 is a schematic diagram of measuring a blood pressure of a user based on a pulse wave signal.

Currently, blood pressure measurement technologies are mainly used to measure a blood pressure of a user by obtaining a physiological signal of the user (hereinafter referred to as the user). The physiological signal of the user includes an electrocardiogram signal and/or a pulse wave signal. The electrocardiogram signal is transmitted when the heart of the user beats, and the pulse wave signal is formed when blood of the user flows in a blood vessel and interacts with the blood vessel. FIG. 1 is a schematic diagram of measuring a blood pressure of a user based on a pulse wave signal. As shown in FIG. 1, a blood flow parameter of blood that flows in the blood vessel is analyzed and obtained based on the pulse wave signal and by using the Photoplethysmography. A pulsatility change of a blood volume of periphery capillaries that is generated with heartbeats is obtained by using the Photoplethysmography (Photoplethysmography, PPG for short), and a PPG signal is further obtained. The PPG is a simple and low-cost optical measurement technology that may be used to detect a blood volume change in a tissue blood vessel. In an implementation principle of measuring a blood pressure based on a pulse wave signal, two photoplethysmography sensors (a PPG 1 and a PPG 2 in FIG. 1) are respectively placed on skin of a brachial artery (a location 1 in FIG. 1) and a middle finger artery (a location 2 in FIG. 1) of the user, a distance between the two arteries may be obtained by measuring a distance between the brachial artery and the middle finger artery, that is, a distance between the two arteries that the pulse wave passes through, a pulse wave transit time (Pulse Transit Time, PTT) may be obtained by measuring a time point T1 when the pulse wave is at the location 1 and a time point T2 when the pulse wave is at the location 2, a pulse wave velocity (Pulse Wave Velocity, PWV) is calculated based on the distance between the two arteries and the pulse wave transit time, and the blood pressure of the user is measured based on a linear relationship between the PWV and the blood pressure.

Figure 2:
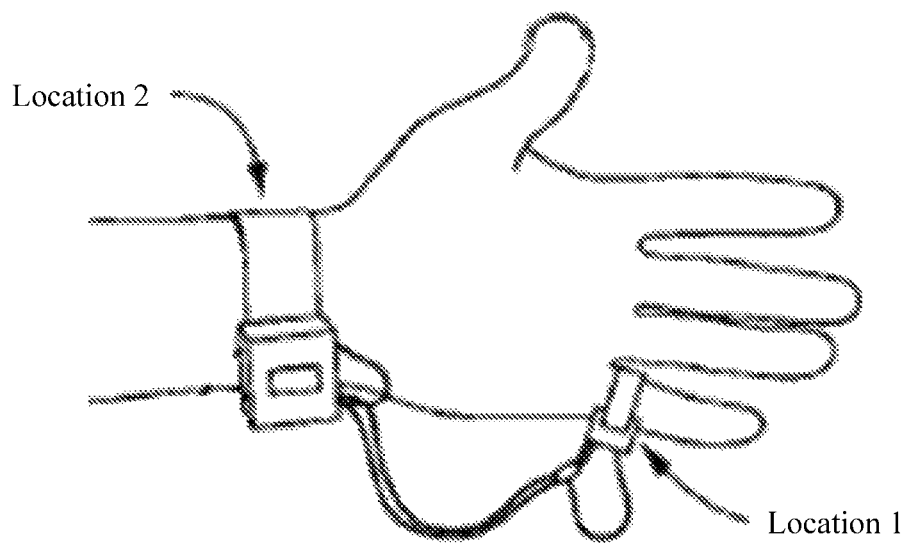
FIG. 2 is a schematic diagram of measuring a blood pressure of a user based on a pulse wave signal and an electrocardiogram signal.
Figure 3:
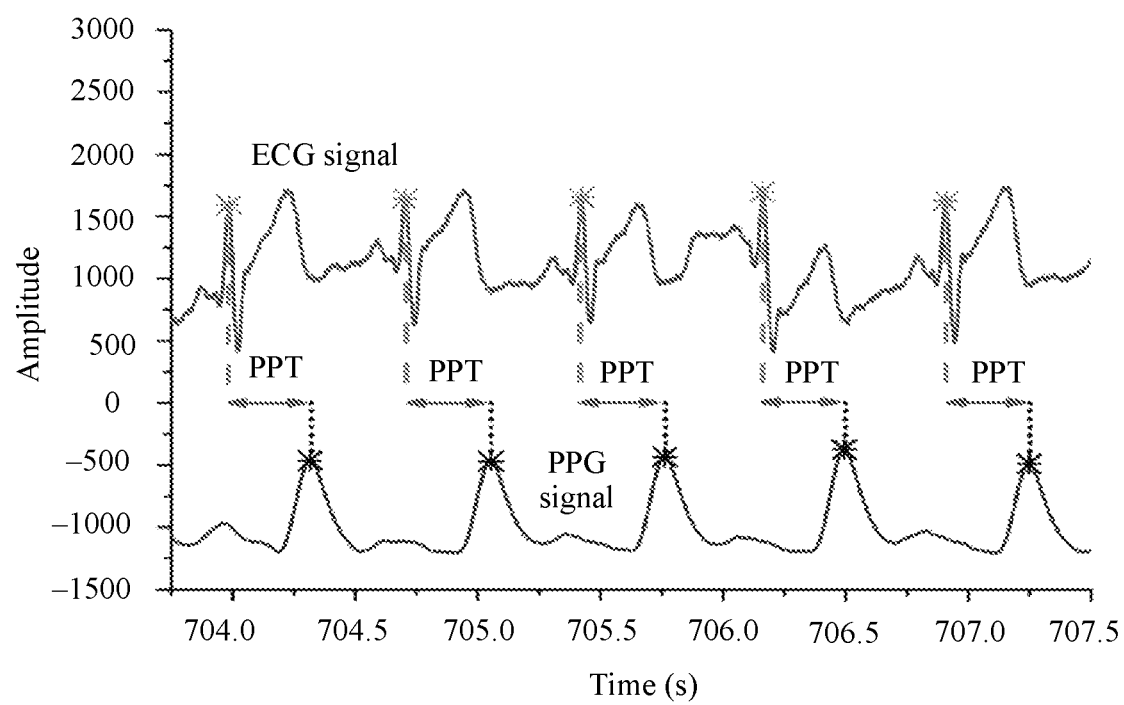
FIG. 3 is a schematic diagram of obtaining a PPT based on a pulse wave signal and an electrocardiogram signal.

FIG. 2 is a schematic diagram of measuring a blood pressure of a user based on a pulse wave signal and an electrocardiogram signal. FIG. 3 is a schematic diagram of obtaining a PPT based on a pulse wave signal and an electrocardiogram signal. As shown in FIG. 2 and FIG. 3, the blood pressure of the user is measured based on a reference point of an electrocardiogram signal and a reference point on a pulse wave signal detected in a same cardiac cycle. In an implementation principle of measuring a blood pressure based on a pulse wave signal and an electrocardiogram signal, a photoplethysmography sensor is placed on skin of a little finger artery of the user, and a pressure pulse wave sensor is placed on skin of a wrist of the user, a distance between the two arteries is obtained by measuring a distance between the little finger artery (a location 1 in FIG. 2) and the wrist (a location 2 in FIG. 2) of the user, the PPT may be obtained by measuring a time point when the pulse wave is at the location 1 and a time point when the electrocardiogram signal is at the location 2, a PWV is calculated based on the distance between the two arteries and the PTT, and the blood pressure of the user is measured based on a linear relationship between the PWV and the blood pressure.

Specific embodiments are used below to describe in detail the technical solutions of the present invention. The following several specific embodiments may be combined with each other, and a same or similar concept or process may not be described repeatedly in some embodiments.

Figure 4A:
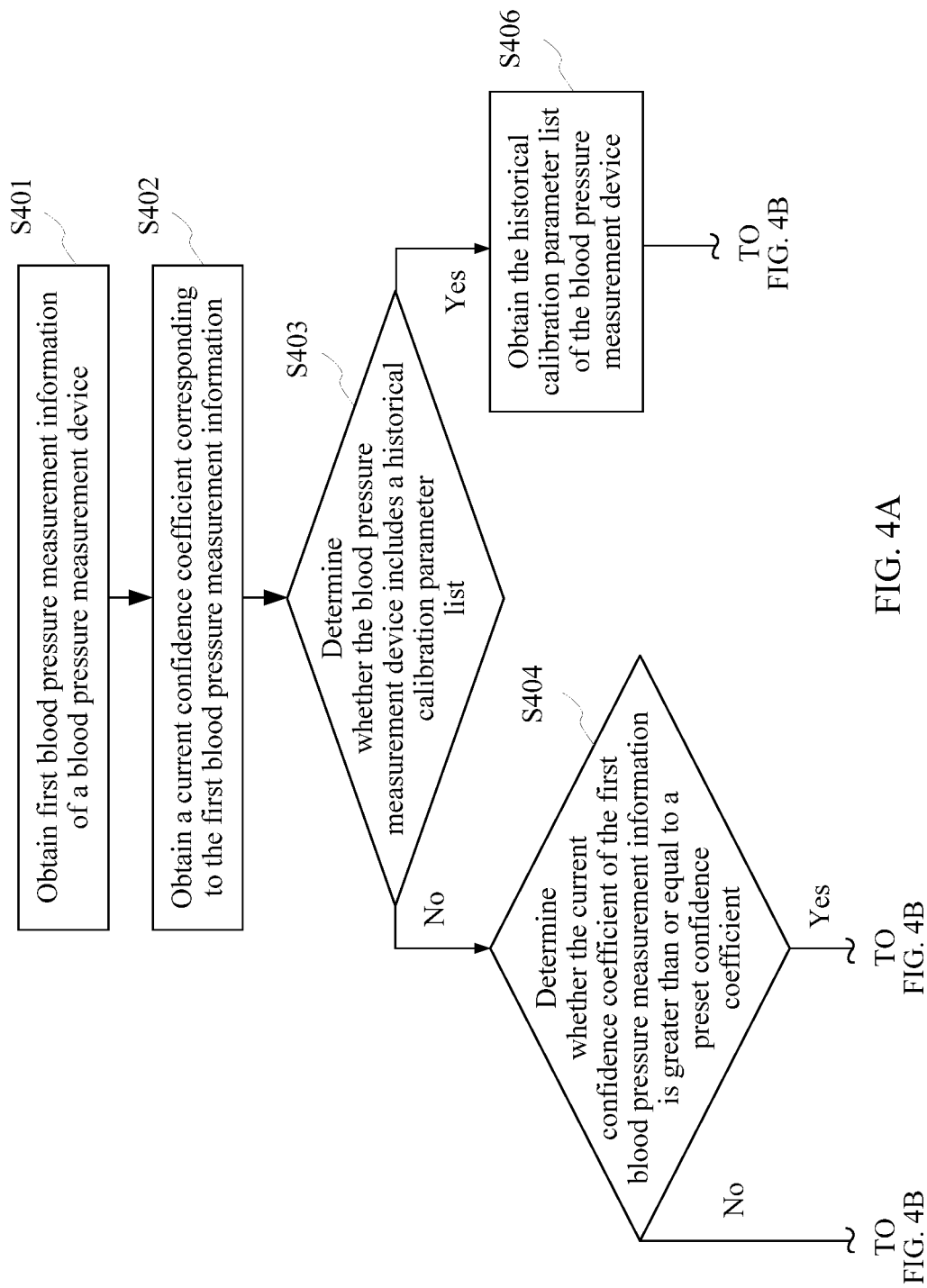
FIG. 4A to FIG. 4C are a flowchart of a method for calibrating a blood pressure measurement device according to an embodiment of the present invention.
Figure 4B:
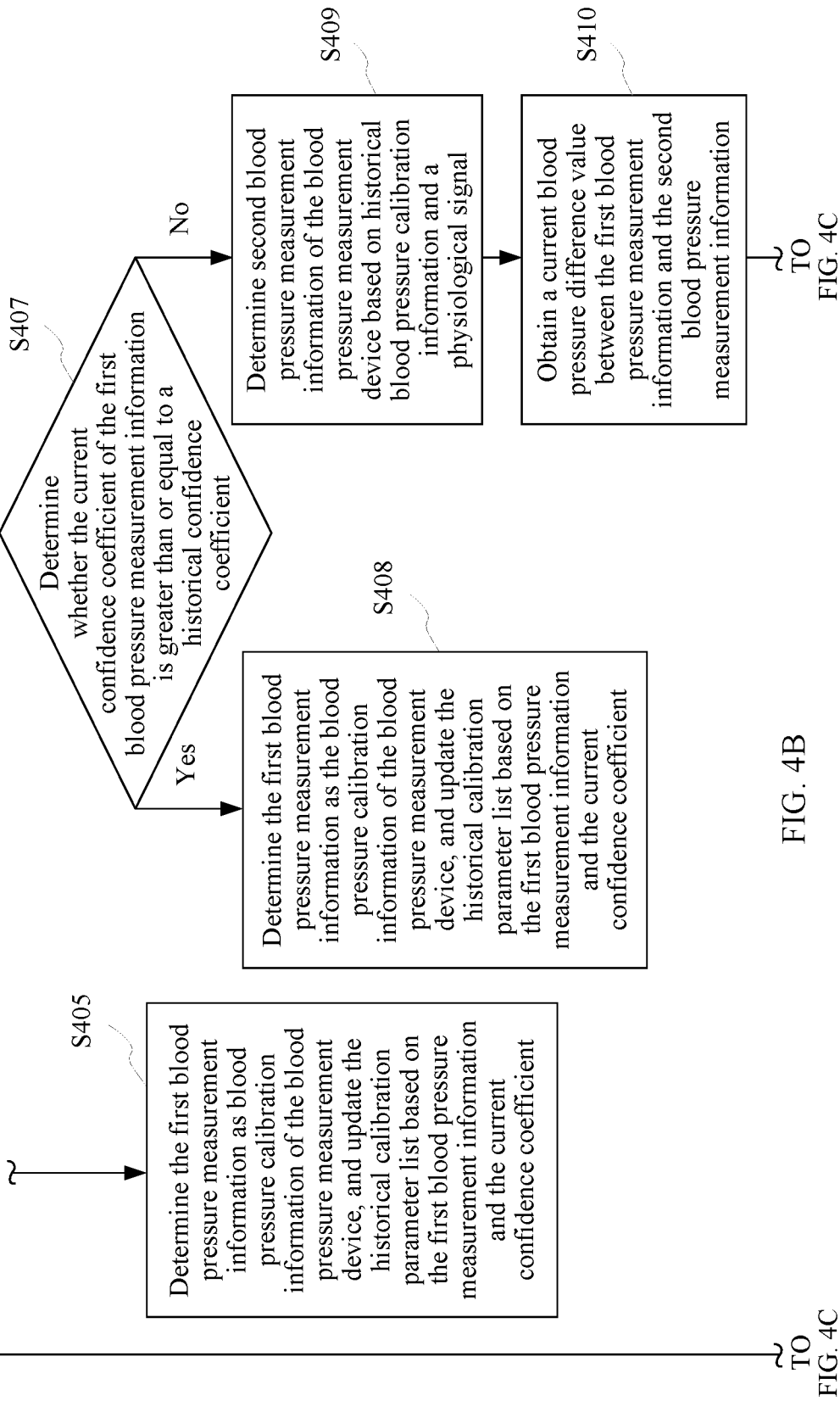
Figure 4C:
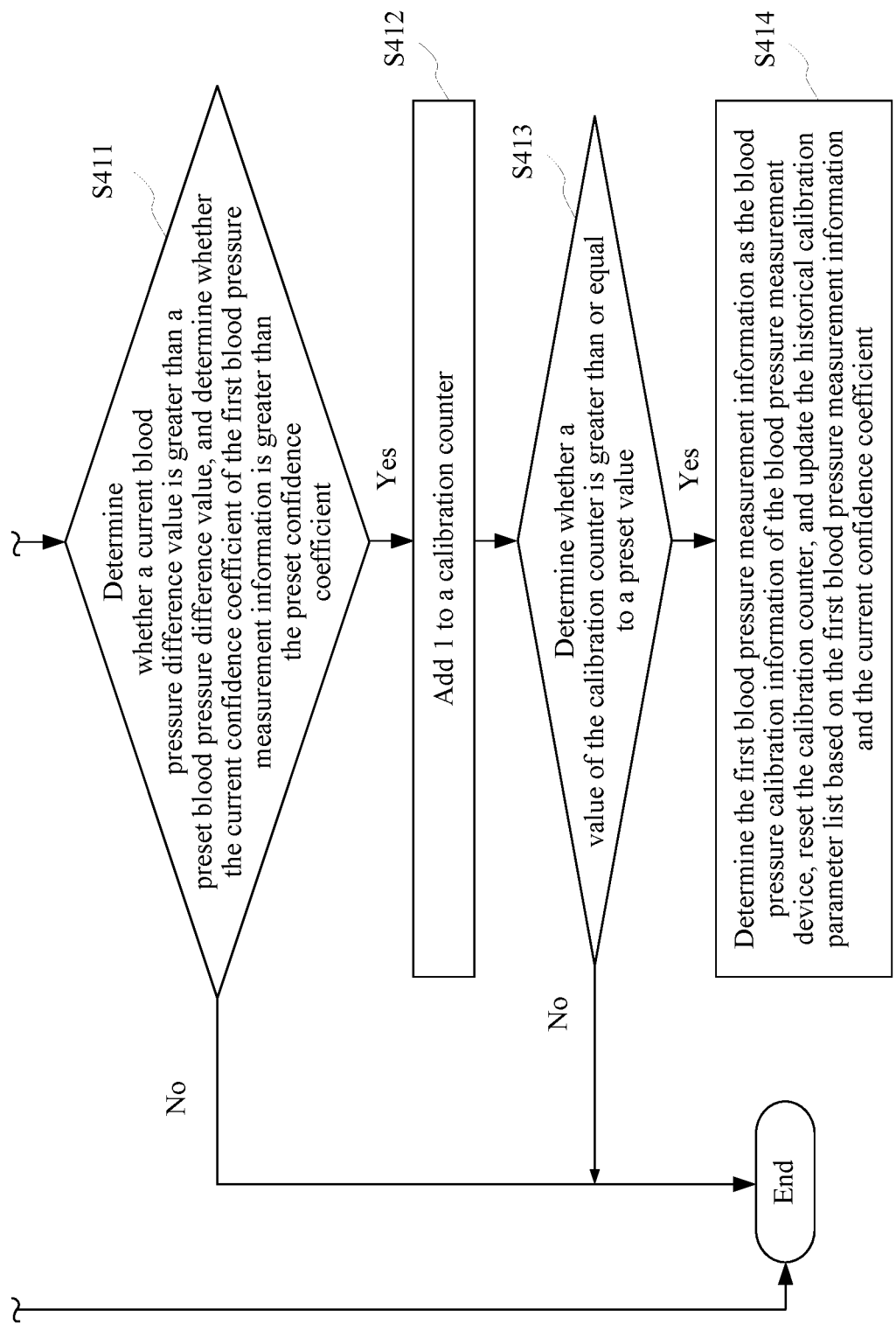

FIG. 4A to FIG. 4C are a flowchart of a method for calibrating a blood pressure measurement device according to an embodiment of the present invention. As shown in FIG. 4, the method for calibrating a blood pressure measurement device according to an embodiment of the present invention includes the following steps.

S401. Obtain first blood pressure measurement information of the blood pressure measurement device.

The first blood pressure measurement information includes a first systolic blood pressure value and/or a first diastolic blood pressure value. The first blood pressure measurement information is to-be-calibrated blood pressure information.

Specifically, the method for calibrating a blood pressure measurement device provided in this embodiment of the present invention may be applied to a calibration apparatus of the blood pressure measurement device. The calibration apparatus of the blood pressure measurement device may be terminals such as a mobile phone and a wearable device. In this embodiment, the blood pressure measurement apparatus may include a first calibration measurement module and a second calibration measurement module. The first calibration measurement module is a non-calibration measurement module, and the second calibration measurement module is a calibration measurement module. When a user needs to measure a blood pressure, the user may enable the non-calibration measurement module by inputting personal information of the user (such as a height, a weight, an age, and a gender) and collecting a physiological signal in a specified period (for example, 30 seconds). The non-calibration measurement module may collect at least one physiological signal of the user, such as an electrocardiogram signal and/or a pulse wave signal. First blood pressure measurement information of the user is obtained based on the collected physiological signal and is used as the first blood pressure measurement information of the blood pressure measurement device. The first blood pressure measurement information is blood pressure measurement information of the user that is directly obtained through calculation based on the physiological signal of the user without being calibrated by using any calibration information. The first blood pressure measurement information includes a systolic blood pressure (Systolic pressure, SBP for short) of the user, a diastolic blood pressure (Diastolic pressure, DBP for short) of the user, and a pulse wave transit time (Pulse Transit Time, PTT) of the user. For example, if a measurement result is SBP/DBP=112/72 mmHg (mmHg), it indicates that currently a systolic blood pressure is 112 mmHg, and a diastolic blood pressure is 72 mmHg.

It should be noted that the electrocardiogram signal in this embodiment may be measured by using an optical sensor, a pressure sensor, a sound sensor, a photoelectric sensor, an acceleration sensor, or a displacement sensor, and the pulse wave may be represented by using a photoplethysmogram signal collected by a photoelectric sensor. For information about obtaining, by the non-calibration measurement module, the blood pressure measurement information of the user based on the physiological signal of the user, refer to the foregoing description of FIG. 1 and FIG. 2. This is not limited and details are not described in this embodiment.

It should be noted that when a user needs to measure a blood pressure, the user may enable the non-calibration measurement module by inputting personal information of the user (such as a height, a weight, an age, and a gender) and collecting a physiological signal in a specified period (for example, 30 seconds). The user may set different user accounts, and each user account stores corresponding personal information of a user. For a user that has registered an account, the user may directly use the existing account to log in. For a user that logs in for the first time, the user needs to register a new account name, and input personal information of the user under the account name. When the user inputs the account name to log in to a personal account, the non-calibration measurement module may directly obtain user information stored under the account name, and determine whether historical blood pressure calibration information exists in a calibration database under the account name.

S402. Obtain a current confidence coefficient corresponding to the first blood pressure measurement information.

Specifically, this embodiment of the present invention uses the confidence coefficient to measure accuracy of the first blood pressure measurement information, so as to determine availability of using the first blood pressure measurement information measured by the non-calibration measurement module as calibration information.

Optionally, the current confidence coefficient may be obtained based on at least one of input blood pressure data of the blood pressure measurement device, signal quality of the physiological signal of the blood pressure measurement device, historically input blood pressure data of the blood pressure measurement device, or historical physiological signal data of the blood pressure measurement device.

Specifically, in this embodiment, the current confidence coefficient corresponding to the first blood pressure measurement information (hereinafter referred to as the current confidence coefficient) may be calculated based on one of or a combination of the following: 1. Determining the current confidence coefficient of the first blood pressure measurement information based on input blood pressure data that is of an external user and that is obtained by the non-calibration measurement module; 2. Determining the current confidence coefficient of the first blood pressure measurement information based on historically input blood pressure data that is of the user and that is obtained by the calibration measurement module; 3. Calculating, by the non-calibration measurement module, the signal quality (such as a signal-to-noise ratio, an AC/DC ratio, and signal strength) based on the collected physiological signal of the user, and mapping the signal quality to the current confidence coefficient of the first blood pressure measurement information; 4. Calculating, by the calibration measurement module, the signal quality (such as a signal-to-noise ratio, an AC/DC ratio, and signal strength) based on the historical physiological signal of the user, and mapping the signal quality to the current confidence coefficient of the first blood pressure measurement information; 5. Using a confidence coefficient directly provided by the non-calibration measurement module as the current confidence coefficient of the first blood pressure measurement information; or 6. Calculating, by the current confidence coefficient of the first blood pressure measurement information based on the input blood pressure data, the physiological signal, and the first blood pressure measurement information.

Optionally, the obtaining a current confidence coefficient corresponding to the first blood pressure measurement information includes obtaining a first confidence coefficient Q1 based on the signal quality of the physiological signal, obtaining a second confidence coefficient Q2 based on a difference between the first blood pressure measurement information and the preset calibration information, obtaining a third confidence coefficient Q3 based on similarity between the input blood pressure data and the historically input blood pressure data, and obtaining the current confidence coefficient Q of the first blood pressure measurement information by performing weighted summation on the first confidence coefficient Q1, the second confidence coefficient Q2, and the third confidence coefficient Q3.

Figure 5:
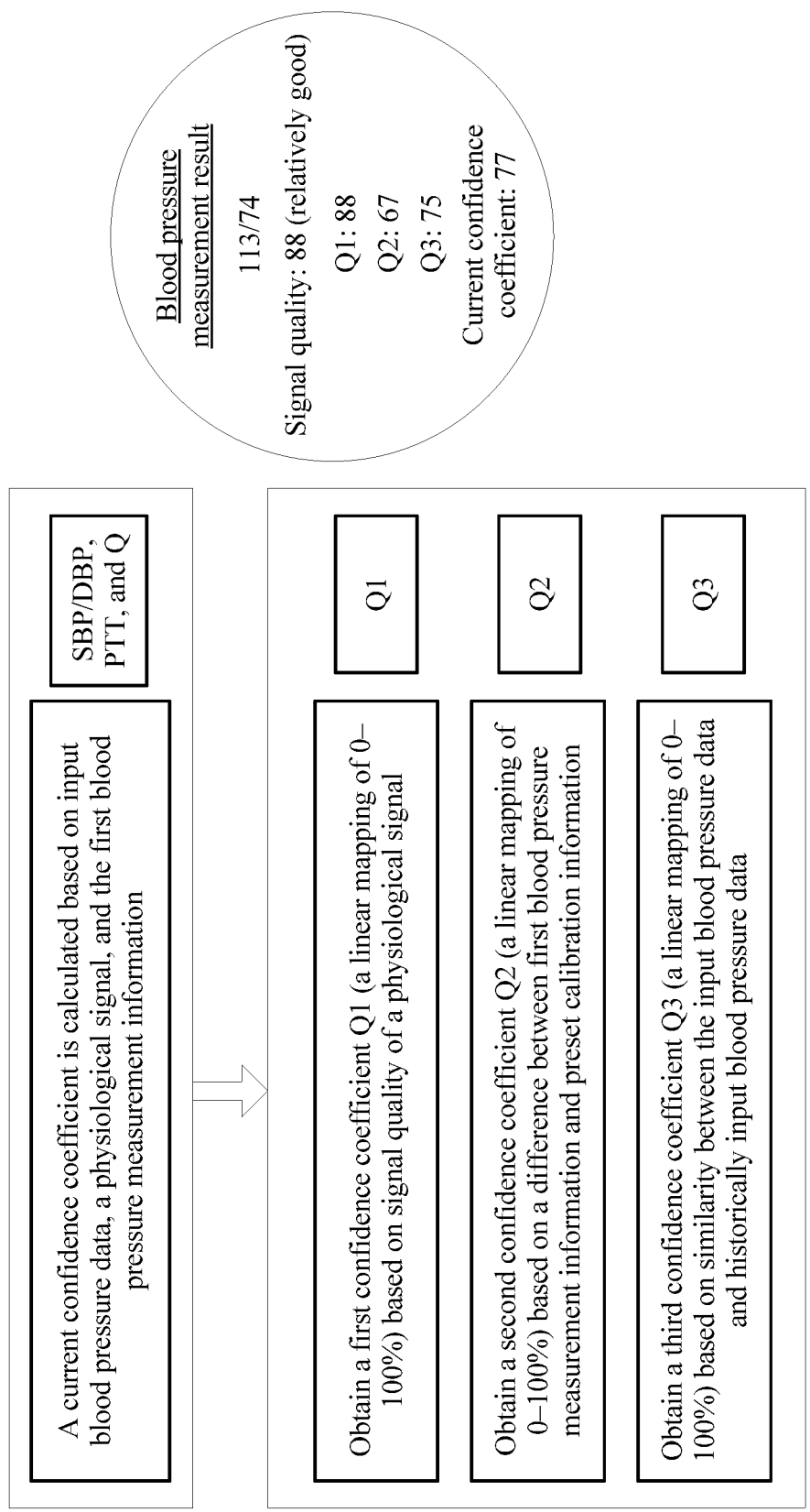
FIG. 5 is a flowchart of calculating a current confidence coefficient of first blood pressure measurement information according to an embodiment of the present invention.

Specifically, in this embodiment, the current confidence coefficient corresponding to the first blood pressure measurement information (hereinafter referred to as the current confidence coefficient) is calculated based on the input blood pressure data, the physiological signal, and the first blood pressure measurement information. FIG. 5 is a flowchart of calculating a current confidence coefficient of first blood pressure measurement information according to an embodiment of the present invention. As shown in FIG. 5, the first confidence coefficient Q1 is obtained based on the signal quality of the physiological signal, the second confidence coefficient Q2 is obtained based on the difference between the first blood pressure measurement information and the historical blood pressure calibration information, and the third confidence coefficient Q3 is obtained based on the similarity between the input blood pressure data and the historically input blood pressure data. The current confidence coefficient Q of the first blood pressure measurement information is obtained based on the first confidence coefficient Q1, the second confidence coefficient Q2, and the third confidence coefficient Q3 and by using formulas $$Q = \sum_{i=1}^{3} \omega_i Q_i \text{ and } \sum_{i=1}^{3} \omega_i = 1.$$

The weighted weight $\omega_i$ may be a fixed value, and in this case, $\omega_i = 1/3$, or $\omega_i$ may be obtained through calculation based on an analytic hierarchy process. This is not limited and details are not described in this embodiment. It should be noted that in this embodiment, alternatively, an arithmetic average value of the first confidence coefficient Q1, the second confidence coefficient Q2, and the third confidence coefficient Q3 may be used as the current confidence coefficient Q of the first blood pressure measurement information.

S403. Determine whether the blood pressure measurement device includes a historical calibration parameter list. If the blood pressure measurement device does not include the historical calibration parameter list, perform S404, or if the blood pressure measurement device includes the historical calibration parameter list, perform S406.

The historical calibration parameter list includes historical blood pressure calibration information and a historical confidence coefficient corresponding to the historical blood pressure calibration information, and the historical blood pressure calibration information includes a historical systolic blood pressure value and/or a historical diastolic blood pressure value.

Specifically, in this embodiment, it is determined whether the blood pressure measurement device includes the historical calibration parameter list, to determine whether calibration of the blood pressure measurement device of the user has a historical calibration scenario or does not have the historical calibration scenario, so as to determine how to set calibration information of the blood pressure measurement device and how to update the calibration information of the blood pressure measurement device in subsequent steps. The historical blood pressure calibration information may include an SBP, a DBP, and a PTT. The historical blood pressure calibration information may be from actual blood pressure data of the user that is input by the user, and in this case, the historical confidence coefficient of the historical blood pressure calibration information is 1. Alternatively, the historical blood pressure calibration information may be from the first blood pressure measurement information measured by the non-calibration measurement module, and in this case, the historical confidence coefficient of the historical blood pressure calibration information is the current confidence coefficient of the first blood pressure measurement information.

It should be noted that a performing sequence between S402 and S403 is interchangeable. S403 may be performed first, and then S402 is performed. This is not limited and details are not described in this embodiment.

S404. Determine whether the current confidence coefficient of the first blood pressure measurement information is greater than or equal to a preset confidence coefficient. If the current confidence coefficient of the first blood pressure measurement information is greater than or equal to the preset confidence coefficient, perform S405, or if the current confidence coefficient of the first blood pressure measurement information is less than the preset confidence coefficient, the process ends.

Specifically, when it is detected in S403 that no historical blood pressure calibration information exists in the calibration database, the first blood pressure measurement information may be directly used as the calibration information for calibration in this embodiment. Before the first blood pressure measurement information is used as the calibration information for calibration, the current confidence coefficient of the first blood pressure measurement information needs to be determined, so as to determine availability of using the first blood pressure measurement information measured by the non-calibration measurement module as the calibration information.

S405. Determine the first blood pressure measurement information as blood pressure calibration information of the blood pressure measurement device, and update the historical calibration parameter list based on the first blood pressure measurement information and the current confidence coefficient.

Specifically, when it is detected in S403 that no historical blood pressure calibration information exists in the calibration database, if the current confidence coefficient of the first blood pressure measurement information is greater than or equal to the preset confidence coefficient, where the preset confidence coefficient may be 90%, the current confidence coefficient of the first blood pressure measurement information is high, an error between the first blood pressure measurement information and an actual blood pressure of the user is relatively small, and accuracy of a blood pressure measured by the non-calibration measurement module is relatively high. In this case, the first blood pressure measurement information may be used as the blood pressure calibration information, that is, the calibration measurement module may calculate the blood pressure based on the first blood pressure measurement information and the collected physiological signal of the user, which may be specifically performing calibration, by using the first blood pressure measurement information, on the blood pressure measurement information obtained based on the physiological signal of the user, so as to output the blood pressure measurement information matching the actual blood pressure of the user, and update the historical calibration parameter list based on the first blood pressure measurement information and the current confidence coefficient. It is detected in S403 that no historical calibration information exists, that is, the historical list is not included. Therefore, it may be understood that the updating the historical calibration parameter list described herein is establishing the historical calibration parameter list. When it is detected in S403 that no historical blood pressure calibration information exists in the calibration database, if the current confidence coefficient of the first blood pressure measurement information is less than the preset confidence coefficient, the process ends and no subsequent process is implemented.

S406. Obtain the historical calibration parameter list of the blood pressure measurement device.

S407. Determine whether the current confidence coefficient of the first blood pressure measurement information is greater than or equal to a historical confidence coefficient. If the current confidence coefficient of the first blood pressure measurement information is greater than or equal to the historical confidence coefficient, perform S408, or if the current confidence coefficient of the first blood pressure measurement information is less than the historical confidence coefficient, perform S409.

Specifically, in S406 and S407, when it is detected in S403 that the historical blood pressure calibration information exists in the calibration database, the historical blood pressure calibration information and the historical calibration parameter list that are of the blood pressure measurement device are obtained, and it is determined whether the current confidence coefficient of the first blood pressure measurement information is greater than or equal to the historical confidence coefficient corresponding to the historical blood pressure calibration information in the historical calibration parameter list, so as to determine whether the first blood pressure measurement information may be used as the calibration information for calibration.

S408. Determine the first blood pressure measurement information as the blood pressure calibration information of the blood pressure measurement device, and update the historical calibration parameter list based on the first blood pressure measurement information and the current confidence coefficient.

Specifically, when it is detected in S403 that the historical blood pressure calibration information exists in the calibration database, and the current confidence coefficient of the first blood pressure measurement information is greater than or equal to the historical confidence coefficient corresponding to the historical blood pressure calibration information, the current confidence coefficient of the first blood pressure measurement information is high, the error between the first blood pressure measurement information and the actual blood pressure of the user is relatively small, and the accuracy of the blood pressure measured by the non-calibration measurement module is relatively high. In this case, the first blood pressure measurement information may be used as the blood pressure calibration information, that is, the calibration measurement module may calculate the blood pressure based on the first blood pressure measurement information and the collected physiological signal of the user, which may be specifically performing calibration, by using the first blood pressure measurement information, on the blood pressure measurement information obtained based on the physiological signal of the user, so as to output the blood pressure measurement information matching the actual blood pressure of the user, and update the historical calibration parameter list based on the first blood pressure measurement information and the current confidence coefficient.

S409. Determine second blood pressure measurement information of the blood pressure measurement device based on historical blood pressure calibration information and a physiological signal.

The second blood pressure measurement information includes a second systolic blood pressure value and/or a second diastolic blood pressure value.

Further, when the first blood pressure measurement information of the blood pressure measurement device is obtained in S401, the physiological signal in the blood pressure measurement device is obtained, where the physiological signal includes an electrocardiogram signal of a user and/or a pulse wave signal of the user.

Specifically, when it is detected in S403 that the historical blood pressure calibration information exists in the calibration database, and the current confidence coefficient of the first blood pressure measurement information is less than the historical confidence coefficient, the second blood pressure measurement information of the blood pressure measurement device is determined based on the historical blood pressure calibration information and the physiological signal in this embodiment, which is specifically obtaining the second blood pressure measurement information after performing calibration, by using the historical blood pressure calibration information, on the blood pressure measurement information of the user that is obtained based on the physiological signal.

S410. Obtain a current blood pressure difference value between the first blood pressure measurement information and the second blood pressure measurement information.

Specifically, the current blood pressure difference value between the first blood pressure measurement information and the second blood pressure measurement information may be determined based on a current blood pressure difference value between the first systolic blood pressure value and the second systolic blood pressure value, or the current blood pressure difference value between the first blood pressure measurement information and the second blood pressure measurement information may be determined based on a current blood pressure difference value between the first diastolic blood pressure value and the second diastolic blood pressure value, or the current blood pressure difference value between the first blood pressure measurement information and the second blood pressure measurement information may be determined based on a ratio of the first systolic blood pressure value to the first diastolic blood pressure value, and a ratio of the second systolic blood pressure value to the second diastolic blood pressure value.

The current blood pressure difference value between the first blood pressure measurement information and the second blood pressure measurement information is determined, so as to determine whether the first blood pressure measurement information may be used as the calibration information for calibration.

S411. Determine whether a current blood pressure difference value is greater than a preset blood pressure difference value, and determine whether the current confidence coefficient of the first blood pressure measurement information is greater than the preset confidence coefficient. If the current blood pressure difference value is greater than or equal to the preset blood pressure difference value, and the current confidence coefficient of the first blood pressure measurement information is greater than or equal to the preset confidence coefficient, perform S412, or if the current blood pressure difference value is less than the preset blood pressure difference value, and the current confidence coefficient of the first blood pressure measurement information is less than the preset confidence coefficient, the process ends.

Specifically, when it is detected in S403 that the historical blood pressure calibration information exists in the calibration database, and the current confidence coefficient of the first blood pressure measurement information is less than the historical confidence coefficient of the historical blood pressure calibration information, it is determined whether the difference value between the first blood pressure measurement information and the second blood pressure measurement information is greater than a preset blood pressure value, and it is determined whether the current confidence coefficient of the first blood pressure measurement information is greater than the preset confidence coefficient, so as to determine whether accuracy of the first blood pressure measurement information measured by the non-calibration measurement module is higher than accuracy of the second blood pressure measurement information measured by the calibration measurement module. Therefore, availability of using the first blood pressure measurement information as the calibration information is determined.

S412. Add 1 to a calibration counter.

Specifically, the calibration counter may be provided in this embodiment of the present invention. When it is determined in S410 that the difference value between the first blood pressure measurement information and the second blood pressure measurement information is greater than the preset blood pressure value, and it is determined that the current confidence coefficient of the first blood pressure measurement information is greater than the preset confidence coefficient, 1 is added to the calibration counter.

S413. Determine whether a value of the calibration counter is greater than or equal to a preset value. If the value of the calibration counter is greater than or equal to the preset value, perform S414, or if the value of the calibration counter is less than the preset value, the process ends.

Specifically, in this embodiment, the value of the calibration counter is compared with the preset value. The preset value may be 3, 4, 5, or the like. For example, in this embodiment, the preset value is set to 5, so as to further determine the availability of using the first blood pressure measurement information as the calibration information.

S414. Determine the first blood pressure measurement information as the blood pressure calibration information of the blood pressure measurement device, reset the calibration counter, and update the historical calibration parameter list based on the first blood pressure measurement information and the current confidence coefficient.

Specifically, when it is determined in S413 that the value of the calibration counter is greater than or equal to the preset value, accuracy of the first blood pressure measurement information is relatively high. The first blood pressure measurement information may be used to perform calibration on blood pressure measurement information of the user, and the historical blood pressure calibration information is updated with first blood pressure measurement information, the historical confidence coefficient of the historical blood pressure calibration information is updated with the current confidence coefficient of the first blood pressure measurement information, and the calibration counter is reset, so as to implement updating of the calibration database and updating of the calibration counter.

According to the method for calibrating a blood pressure measurement device provided in this embodiment of the present invention, the first blood pressure measurement information that is obtained through direct measurement based on the physiological signal of the user is used as the calibration information, and a non-calibration result is applied to manual calibration measurement. This ensures accuracy of a measured blood pressure, reduces times of using an extra device for manual calibration by the user, and avoids using an extra device to implement calibration of blood pressure measurement information. Consequently, costs of measuring blood pressure information by using the blood pressure measurement apparatus are reduced, and the blood pressure measurement device has a relatively high portability. In addition, it is determined whether the historical blood pressure calibration information exists in the calibration database, two different algorithms are used to determine availability of using the first blood pressure measurement information as the calibration information, and when the historical blood pressure calibration information exists in the calibration database, the historical blood pressure calibration information is updated with the first blood pressure measurement information, so that updated historical blood pressure calibration information matches as much as possible the actual blood pressure of the user to further ensure accuracy of the blood pressure measurement information. When the current confidence coefficient of the first blood pressure measurement information is less than the historical confidence coefficient of the historical blood pressure calibration information, it is determined whether the difference value between the first blood pressure measurement information and the second blood pressure measurement information is greater than the preset blood pressure value, and it is determined whether the current confidence coefficient of the first blood pressure measurement information is greater than a preset threshold, so as to determine whether accuracy of the first blood pressure measurement information measured by the non-calibration measurement module is higher than accuracy of the second blood pressure measurement information measured by the calibration measurement module. Therefore, availability of using the first blood pressure measurement information as the calibration information is determined.

Figure 6:
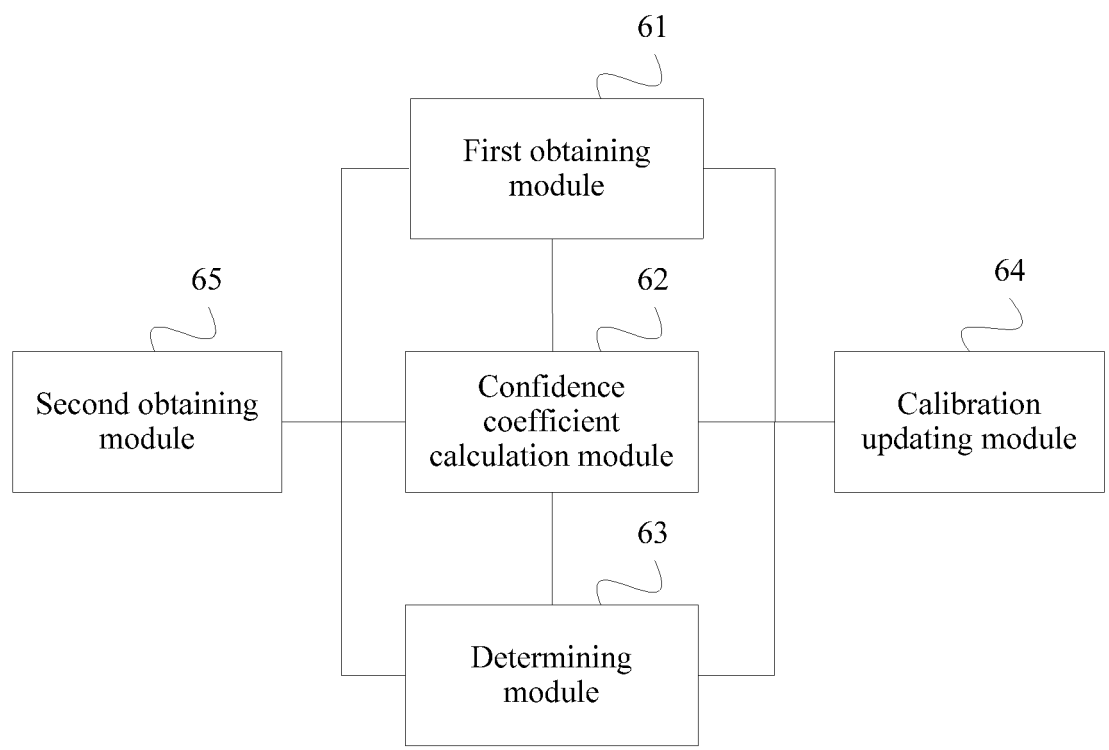
FIG. 6 is a schematic structural diagram of a blood pressure measurement device according to an embodiment of the present invention.

FIG. 6 is a schematic structural diagram of a blood pressure measurement device according to an embodiment of the present invention. As shown in FIG. 6, the blood pressure measurement device includes a first obtaining module 61, a confidence coefficient calculation module 62, a determining module 63, and a calibration updating module 64.

The first obtaining module 61 is configured to obtain first blood pressure measurement information of the blood pressure measurement device, where the first blood pressure measurement information includes a first systolic blood pressure value and/or a first diastolic blood pressure value.

The confidence coefficient calculation module 62 is configured to obtain a current confidence coefficient corresponding to the first blood pressure measurement information.

The determining module 63 is configured to determine whether the blood pressure measurement device includes a historical calibration parameter list, where the historical calibration parameter list includes historical blood pressure calibration information and a historical confidence coefficient corresponding to the historical blood pressure calibration information, and the historical blood pressure calibration information includes a historical systolic blood pressure value and/or a historical diastolic blood pressure value.

The calibration updating module 64 is configured to, when the determining module 63 determines that the blood pressure measurement device includes the historical calibration parameter list, and the current confidence coefficient is greater than or equal to a preset confidence coefficient, or is greater than or equal to the historical confidence coefficient, determine the first blood pressure measurement information as blood pressure calibration information of the blood pressure measurement device, and update the historical calibration parameter list based on the first blood pressure measurement information and the current confidence coefficient.

The blood pressure measurement device in this embodiment of the present invention may perform the technical solution shown in the foregoing method embodiment. The implementation principles and beneficial effects of the device are similar to those of the technical solution, and are not described herein again.

In a possible implementation, the blood pressure measurement device further includes a second obtaining module 65.

The second obtaining module 65 is configured to, when the determining module 63 determines that the blood pressure measurement device does not include the historical calibration parameter list, obtain a physiological signal of the blood pressure measurement device, where the physiological signal includes an electrocardiogram signal of a user and/or a pulse wave signal of the user.

The first obtaining module 61 is further configured to, when the current confidence coefficient is less than the historical confidence coefficient, determine second blood pressure measurement information of the blood pressure measurement device based on the historical blood pressure calibration information and the physiological signal, where the second blood pressure measurement information includes a second systolic blood pressure value and/or a second diastolic blood pressure value.

The calibration updating module 64 is further configured to, obtain a current blood pressure difference value between the first blood pressure measurement information and the second blood pressure measurement information, when the current blood pressure difference value is greater than or equal to a preset blood pressure difference value, and the current confidence coefficient is greater than or equal to the preset confidence coefficient, add 1 to a calibration counter, and when a value of the calibration counter is greater than or equal to a preset value, determine the first blood pressure measurement information as blood pressure calibration information of the blood pressure measurement device, reset the calibration counter, and update the historical calibration parameter list based on the first blood pressure measurement information and the current confidence coefficient.

In another possible implementation, the calibration updating module 64 is specifically configured to determine the current blood pressure difference value based on the first systolic blood pressure value and the second systolic blood pressure value, or determine the current blood pressure difference value based on the first diastolic blood pressure value and the second diastolic blood pressure value, or determine the current blood pressure difference value based on a ratio of the first systolic blood pressure value to the first diastolic blood pressure value, and a ratio of the second systolic blood pressure value to the second diastolic blood pressure value.

In another possible implementation, the confidence coefficient calculation module 62 is specifically configured to obtain the current confidence coefficient based on at least one of input blood pressure data of the blood pressure measurement device, signal quality of the physiological signal of the blood pressure measurement device, historically input blood pressure data of the blood pressure measurement device, or historical physiological signal data of the blood pressure measurement device.

In another possible implementation, the confidence coefficient calculation module 62 is specifically configured to obtain a first confidence coefficient based on the signal quality of the physiological signal, obtain a second confidence coefficient based on a difference between the first blood pressure measurement information and the historical blood pressure calibration information, obtain a third confidence coefficient based on similarity between the input blood pressure data of the blood pressure measurement device and the historically input blood pressure data of the blood pressure measurement device, and obtain the current confidence coefficient of the first blood pressure measurement information by performing weighted summation on the first confidence coefficient, the second confidence coefficient, and the third confidence coefficient.

The blood pressure measurement device in this embodiment of the present invention may perform the technical solution shown in the foregoing method embodiment. The implementation principles and beneficial effects of the device are similar to those of the technical solution, and are not described herein again.

Figure 7:
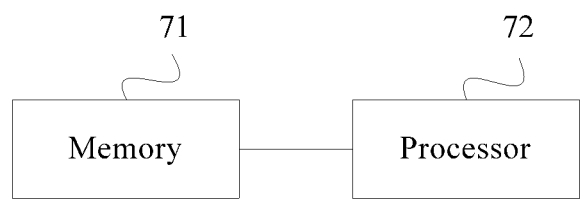
FIG. 7 is a schematic structural diagram of a blood pressure measurement device according to an embodiment of the present invention.

FIG. 7 is a schematic structural diagram of a blood pressure measurement device according to an embodiment of the present invention. As shown in FIG. 7, the blood pressure measurement device provided in this embodiment of the present invention includes a memory 71 and a processor 72.

Specifically, the memory 71 is configured to store an executable instruction. The processor 72 may be a central processing unit (Central Processing Unit, CPU) 72, or an application-specific integrated circuit (Application Specific Integrated Circuit, ASIC), or one or more integrated circuits configured to implement this embodiment of the present invention. The processor 72 is configured to invoke the executable instruction in the memory 71 and perform obtaining first blood pressure measurement information of the blood pressure measurement device and a current confidence coefficient corresponding to the first blood pressure measurement information, where the first blood pressure measurement information includes a first systolic blood pressure value and/or a first diastolic blood pressure value, determining whether the blood pressure measurement device includes a historical calibration parameter list, where the historical calibration parameter list includes historical blood pressure calibration information and a historical confidence coefficient corresponding to the historical blood pressure calibration information, and the historical blood pressure calibration information includes a historical systolic blood pressure value and/or a historical diastolic blood pressure value, and if the blood pressure measurement device includes the historical calibration parameter list, and the current confidence coefficient is greater than or equal to a preset confidence coefficient, or is greater than or equal to the historical confidence coefficient, determining the first blood pressure measurement information as blood pressure calibration information of the blood pressure measurement device, and updating the historical calibration parameter list based on the first blood pressure measurement information and the current confidence coefficient.

The blood pressure measurement device in this embodiment of the present invention may perform the technical solution shown in the foregoing method embodiment. The implementation principles and beneficial effects of the device are similar to those of the technical solution, and are not described herein again.

In a possible implementation, the processor 72 is specifically configured to, if the blood pressure measurement device does not include the historical calibration parameter list, obtain a physiological signal of the blood pressure measurement device, where the physiological signal includes an electrocardiogram signal of a user and/or a pulse wave signal of the user, when the current confidence coefficient is less than the historical confidence coefficient, determine second blood pressure measurement information of the blood pressure measurement device based on the historical blood pressure calibration information and the physiological signal, where the second blood pressure measurement information includes a second systolic blood pressure value and/or a second diastolic blood pressure value, obtain a current blood pressure difference value between the first blood pressure measurement information and the second blood pressure measurement information, and if the current blood pressure difference value is greater than or equal to a preset blood pressure difference value, and the current confidence coefficient is greater than or equal to the preset confidence coefficient, add 1 to a calibration counter, and when a value of the calibration counter is greater than or equal to a preset value, determine the first blood pressure measurement information as blood pressure calibration information of the blood pressure measurement device, reset the calibration counter, and update the historical calibration parameter list based on the first blood pressure measurement information and the current confidence coefficient.

In another possible implementation, the processor 72 is specifically configured to determine the current blood pressure difference value based on the first systolic blood pressure value and the second systolic blood pressure value, or determine the current blood pressure difference value based on the first diastolic blood pressure value and the second diastolic blood pressure value, or determine the current blood pressure difference value based on a ratio of the first systolic blood pressure value to the first diastolic blood pressure value, and a ratio of the second systolic blood pressure value to the second diastolic blood pressure value.

In another possible implementation, the processor 72 is specifically configured to obtain the current confidence coefficient based on at least one of input blood pressure data of the blood pressure measurement device, signal quality of the physiological signal of the blood pressure measurement device, historically input blood pressure data of the blood pressure measurement device, or historical physiological signal data of the blood pressure measurement device.

In another possible implementation, the processor 72 is specifically configured to obtain a first confidence coefficient based on the signal quality of the physiological signal, obtain a second confidence coefficient based on a difference between the first blood pressure measurement information and the historical blood pressure calibration information, obtain a third confidence coefficient based on similarity between the input blood pressure data of the blood pressure measurement device and the historically input blood pressure data of the blood pressure measurement device, and obtain the current confidence coefficient of the first blood pressure measurement information by performing weighted summation on the first confidence coefficient, the second confidence coefficient, and the third confidence coefficient.

The blood pressure measurement device in this embodiment of the present invention may perform the technical solution shown in the foregoing method embodiment. The implementation principles and beneficial effects of the device are similar to those of the technical solution, and are not described herein again.

Finally, it should be noted that the foregoing embodiments are merely intended for describing the technical solutions of the present invention, but not for limiting the present invention. Although the present invention is described in detail with reference to the foregoing embodiments, a person of ordinary skill in the art should understand that they may still make modifications to the technical solutions described in the foregoing embodiments or make equivalent replacements to some or all technical features thereof, without departing from the scope of the technical solutions of the embodiments of the present invention.

What is claimed is:

1. A method by a blood pressure measurement device, the method comprising:

obtaining first blood pressure measurement information of a user measured by the blood pressure measurement device and a current confidence coefficient corresponding to the first blood pressure measurement information, the current confidence coefficient based at least in part on a signal quality of a physiological signal of the blood pressure measurement device, wherein the first blood pressure measurement information comprises a first systolic blood pressure value and a first diastolic blood pressure value;

determining whether the blood pressure measurement device comprises a historical calibration parameter list, wherein the historical calibration parameter list comprises historical blood pressure calibration information of the user and a historical confidence coefficient corresponding to the historical blood pressure calibration information, and wherein the historical blood pressure calibration information comprises a historical systolic blood pressure value and a historical diastolic blood pressure value; and in response to the blood pressure measurement device comprising the historical calibration parameter list, and the current confidence coefficient being greater than or equal to a preset confidence coefficient or being greater than or equal to the historical confidence coefficient:

determining the first blood pressure measurement information as blood pressure calibration information of the blood pressure measurement device; and updating the historical calibration parameter list according to the first blood pressure measurement information and the current confidence coefficient; and calibrating, based on the updated historical calibration parameter list, a blood pressure measurement of the user that is measured by the blood pressure measurement device; and wherein, in response to the blood pressure measurement device comprising the historical calibration parameter list, the method further comprises:

obtaining the physiological signal of the blood pressure measurement device, wherein the physiological signal comprises an electrocardiogram signal of the user or a pulse wave signal of the user;

determining, in response to the current confidence coefficient being less than the historical confidence coefficient, second blood pressure measurement information of the blood pressure measurement device according to the historical blood pressure calibration information and the physiological signal, wherein the second blood pressure measurement information comprises a second systolic blood pressure value or a second diastolic blood pressure value;

obtaining a current blood pressure difference value between the first blood pressure measurement information and the second blood pressure measurement information;

adding 1 to a value of a calibration counter in response to the current blood pressure difference value being greater than or equal to a preset blood pressure difference value, and further in response to the current confidence coefficient being greater than or equal to the preset confidence coefficient; and in response to the value of the calibration counter is greater than or equal to a preset value:
determining the first blood pressure measurement information as the blood pressure calibration information of the blood pressure measurement device;
resetting the calibration counter; and
updating the historical calibration parameter list according to the first blood pressure measurement information and the current confidence coefficient.

2. The method according to claim 1, wherein the obtaining the current blood pressure difference value between the first blood pressure measurement information and the second blood pressure measurement information comprises:
determining the current blood pressure difference value according to the first systolic blood pressure value and the second systolic blood pressure value.

3. The method according to claim 1, wherein the obtaining the current confidence coefficient corresponding to the first blood pressure measurement information comprises:
obtaining the current confidence coefficient according to at least one of input blood pressure data of the blood pressure measurement device, the signal quality of the physiological signal of the blood pressure measurement device, historically input blood pressure data of the blood pressure measurement device, or historical physiological signal data of the blood pressure measurement device.

4. The method according to claim 1, wherein the obtaining the current confidence coefficient corresponding to the first blood pressure measurement information comprises:
obtaining a first confidence coefficient according to the signal quality of the physiological signal;
obtaining a second confidence coefficient according to a difference between the first blood pressure measurement information and the historical blood pressure calibration information;
obtaining a third confidence coefficient according to a similarity between input blood pressure data of the blood pressure measurement device and historically input blood pressure data of the blood pressure measurement device; and
obtaining the current confidence coefficient of the first blood pressure measurement information by performing weighted summation on the first confidence coefficient, the second confidence coefficient, and the third confidence coefficient.

5. The method according to claim 1, wherein the obtaining the current blood pressure difference value between the first blood pressure measurement information and the second blood pressure measurement information comprises:

determining the current blood pressure difference value according to the first diastolic blood pressure value and the second diastolic blood pressure value.

6. The method according to claim 1, wherein the obtaining the current blood pressure difference value between the first blood pressure measurement information and the second blood pressure measurement information comprises:
determining the current blood pressure difference value according to a ratio of the first systolic blood pressure value to the first diastolic blood pressure value, and a ratio of the second systolic blood pressure value to the second diastolic blood pressure value.

7. A blood pressure measurement device, comprising:
one or more processors; and
a non-transitory computer-readable storage medium storing a program to be executed by the one or more processors, the program including instructions that, when executed by the one or more processors, cause the blood pressure measurement device to:
obtain first blood pressure measurement information of a user measured by the blood pressure measurement device and a current confidence coefficient corresponding to the first blood pressure measurement information, the current confidence coefficient based at least in part on a signal quality of a physiological signal of the blood pressure measurement device, wherein the first blood pressure measurement information comprises a first systolic blood pressure value and a first diastolic blood pressure value;
determine whether the blood pressure measurement device comprises a historical calibration parameter list, wherein the historical calibration parameter list comprises historical blood pressure calibration information of the user and a historical confidence coefficient corresponding to the historical blood pressure calibration information, and the historical blood pressure calibration information comprises a historical systolic blood pressure value and a historical diastolic blood pressure value; and
in response to the blood pressure measurement device comprising the historical calibration parameter list, and the current confidence coefficient being greater than or equal to a preset confidence coefficient, or being greater than or equal to the historical confidence coefficient:
determine the first blood pressure measurement information as blood pressure calibration information of the blood pressure measurement device; and
update the historical calibration parameter list according to the first blood pressure measurement information and the current confidence coefficient; and
calibrating, based on the updated historical calibration parameter list, a blood pressure measurement of the user that is measured by the blood pressure measurement device; and
wherein, in response to the blood pressure measurement device comprising the historical calibration parameter list, the program further includes instructions to:
obtain the physiological signal of the blood pressure measurement device, wherein the physiological signal comprises an electrocardiogram signal of the user or a pulse wave signal of the user;
determine, in response to the current confidence coefficient being less than the historical confidence coefficient, second blood pressure measurement information of the blood pressure measurement device according to the historical blood pressure calibration information and the physiological signal, wherein the second blood pressure measurement information comprises a second systolic blood pressure value or a second diastolic blood pressure value;

obtain a current blood pressure difference value between the first blood pressure measurement information and the second blood pressure measurement information;

add 1 to a value of a calibration counter in response to the current blood pressure difference value being greater than or equal to a preset blood pressure difference value, and further in response to the current confidence coefficient being greater than or equal to the preset confidence coefficient; and in response to the value of the calibration counter being greater than or equal to a preset value:
determine the first blood pressure measurement information as the blood pressure calibration information of the blood pressure measurement device;
reset the calibration counter; and
update the historical calibration parameter list according to the first blood pressure measurement information and the current confidence coefficient.

8. The blood pressure measurement device according to claim 7, wherein the instructions to obtain the current blood pressure difference value between the first blood pressure measurement information and the second blood pressure measurement information further include instructions to:
determine the current blood pressure difference value according to the first systolic blood pressure value and the second systolic blood pressure value.

9. The blood pressure measurement device according to claim 7, wherein the instructions to obtain the current confidence coefficient corresponding to the first blood pressure measurement information further include instructions to:
obtain the current confidence coefficient according to at least one of input blood pressure data of the blood pressure measurement device, the signal quality of the physiological signal of the blood pressure measurement device, historically input blood pressure data of the blood pressure measurement device, or historical physiological signal data of the blood pressure measurement device.

10. The blood pressure measurement device according to claim 7, wherein the instructions to obtain the current confidence coefficient corresponding to the first blood pressure measurement information further include instructions to:
obtain a first confidence coefficient according to the signal quality of the physiological signal;
obtain a second confidence coefficient according to a difference between the first blood pressure measurement information and the historical blood pressure calibration information;
obtain a third confidence coefficient according to a similarity between input blood pressure data of the blood pressure measurement device and historically input blood pressure data of the blood pressure measurement device; and
obtain the current confidence coefficient of the first blood pressure measurement information by performing weighted summation on the first confidence coefficient, the second confidence coefficient, and the third confidence coefficient.

11. The blood pressure measurement device according to claim 7, wherein the instructions to obtain the current blood pressure difference value between the first blood pressure measurement information and the second blood pressure measurement information further include instructions to:
determine the current blood pressure difference value according to the first diastolic blood pressure value and the second diastolic blood pressure value.

12. The blood pressure measurement device according to claim 7, wherein the instructions to obtain the current blood pressure difference value between the first blood pressure measurement information and the second blood pressure measurement information further include instructions to:
determine the current blood pressure difference value according to a ratio of the first systolic blood pressure value to the first diastolic blood pressure value, and a ratio of the second systolic blood pressure value to the second diastolic blood pressure value.

13. A non-transitory computer-readable medium having instructions stored thereon that, when executed by a blood pressure measurement device, cause the blood pressure measurement device to perform operations, the operations comprising:
obtaining first blood pressure measurement information of a user measured by the blood pressure measurement device and a current confidence coefficient corresponding to the first blood pressure measurement information, the current confidence coefficient based at least in part on a signal quality of a physiological signal of the blood pressure measurement device, wherein the first blood pressure measurement information comprises a first systolic blood pressure value and a first diastolic blood pressure value;
determining whether the blood pressure measurement device comprises a historical calibration parameter list, wherein the historical calibration parameter list comprises historical blood pressure calibration information of the user and a historical confidence coefficient corresponding to the historical blood pressure calibration information, and wherein the historical blood pressure calibration information comprises a historical systolic blood pressure value and a historical diastolic blood pressure value; and
in response to the blood pressure measurement device comprising the historical calibration parameter list, and the current confidence coefficient being greater than or equal to a preset confidence coefficient or being greater than or equal to the historical confidence coefficient:
determining the first blood pressure measurement information as blood pressure calibration information of the blood pressure measurement device; and
updating the historical calibration parameter list according to the first blood pressure measurement information and the current confidence coefficient; and
calibrating, based on the updated historical calibration parameter list, a blood pressure measurement of the user that is measured by the blood pressure measurement device; and
wherein, in response to the blood pressure measurement device comprising the historical calibration parameter list, the operations further comprise:
obtaining the physiological signal of the blood pressure measurement device, wherein the physiological signal comprises an electrocardiogram signal of the user or a pulse wave signal of the user;

determining, in response to the current confidence coefficient being less than the historical confidence coefficient, second blood pressure measurement information of the blood pressure measurement device according to the historical blood pressure calibration information and the physiological signal, wherein the second blood pressure measurement information comprises a second systolic blood pressure value or a second diastolic blood pressure value;

obtaining a current blood pressure difference value between the first blood pressure measurement information and the second blood pressure measurement information;

adding 1 to a value of a calibration counter in response to the current blood pressure difference value being greater than or equal to a preset blood pressure difference value, and further in response to the current confidence coefficient being greater than or equal to the preset confidence coefficient; and in response to the value of the calibration counter is greater than or equal to a preset value:
  determining the first blood pressure measurement information as the blood pressure calibration information of the blood pressure measurement device;
  resetting the calibration counter; and
  updating the historical calibration parameter list according to the first blood pressure measurement information and the current confidence coefficient.

14. The non-transitory computer-readable medium according to claim 13, wherein the obtaining the current blood pressure difference value between the first blood pressure measurement information and the second blood pressure measurement information comprises:
  determining the current blood pressure difference value according to the first systolic blood pressure value and the second systolic blood pressure value.

15. The non-transitory computer-readable medium according to claim 13, wherein the obtaining the current confidence coefficient corresponding to the first blood pressure measurement information comprises:
  obtaining the current confidence coefficient according to at least one of input blood pressure data of the blood pressure measurement device, the signal quality of the physiological signal of the blood pressure measurement device, historically input blood pressure data of the blood pressure measurement device, or historical physiological signal data of the blood pressure measurement device.

16. The non-transitory computer-readable medium according to claim 13, wherein the obtaining the current confidence coefficient corresponding to the first blood pressure measurement information comprises:
  obtaining a first confidence coefficient according to a the signal quality of the physiological signal;
  obtaining a second confidence coefficient according to a difference between the first blood pressure measurement information and the historical blood pressure calibration information;
  obtaining a third confidence coefficient according to a similarity between input blood pressure data of the blood pressure measurement device and historically input blood pressure data of the blood pressure measurement device; and
  obtaining the current confidence coefficient of the first blood pressure measurement information by performing weighted summation on the first confidence coefficient, the second confidence coefficient, and the third confidence coefficient.

17. The non-transitory computer-readable medium according to claim 13, wherein the obtaining the current blood pressure difference value between the first blood pressure measurement information and the second blood pressure measurement information comprises:
  determining the current blood pressure difference value according to the first diastolic blood pressure value and the second diastolic blood pressure value.

* * * * *